United States Patent [19]
Kolbach

[11] 3,973,291
[45] Aug. 10, 1976

[54] METHOD FOR FORMING FIBROUS PADS
[75] Inventor: Charles G. Kolbach, Media, Pa.
[73] Assignee: Scott Paper Company, Philadelphia, Pa.
[22] Filed: May 31, 1974
[21] Appl. No.: 475,034

Related U.S. Application Data
[60] Division of Ser. No. 237,963, March 24, 1972, Pat. No. 3,846,871, which is a continuation-in-part of Ser. No. 67,862, Aug. 28, 1970, abandoned.

[52] U.S. Cl.................................. 19/148; 19/156.3
[51] Int. Cl.²......................................... D01G 25/00
[58] Field of Search............... 19/156.3, 156.4, 144, 19/148, 145, 155; 425/80–83; 128/284

[56]          References Cited
              UNITED STATES PATENTS

| | | | |
|---|---|---|---|
| 2,068,203 | 1/1937 | Simpson............................ | 425/80 X |
| 2,949,646 | 8/1960 | Clark.................................. | 19/155 |
| 3,518,726 | 7/1970 | Banks............................ | 19/144.55 |
| 3,598,680 | 8/1971 | Lee..................................... | 425/82 |
| 3,641,627 | 2/1972 | Lee et al............................ | 19/156.3 |
| 3,717,905 | 2/1973 | Furbeck......................... | 19/156.3 X |
| 3,766,922 | 10/1973 | Krusko.............................. | 128/284 |

*Primary Examiner*—Dorsey Newton
*Attorney, Agent, or Firm*—Martin L. Faigus; William J. Foley

[57]              ABSTRACT

A method for forming discrete fibrous pads including the steps of entraining fibers in air to form an air-suspension of fibers and directing the suspension selectively to different predetermined regions of a pad-formation assembly to form discrete fibrous pads on the assembly.

8 Claims, 21 Drawing Figures

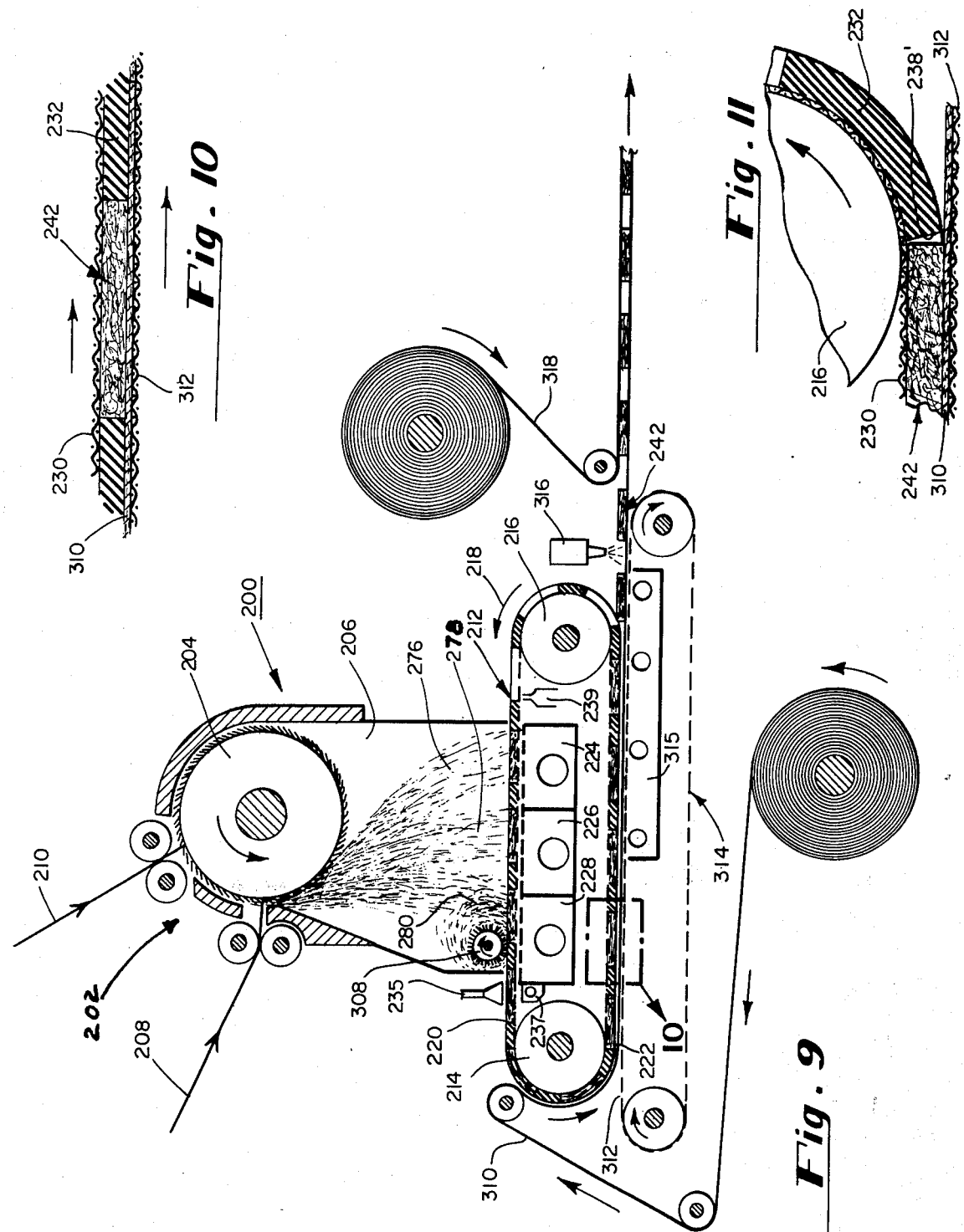

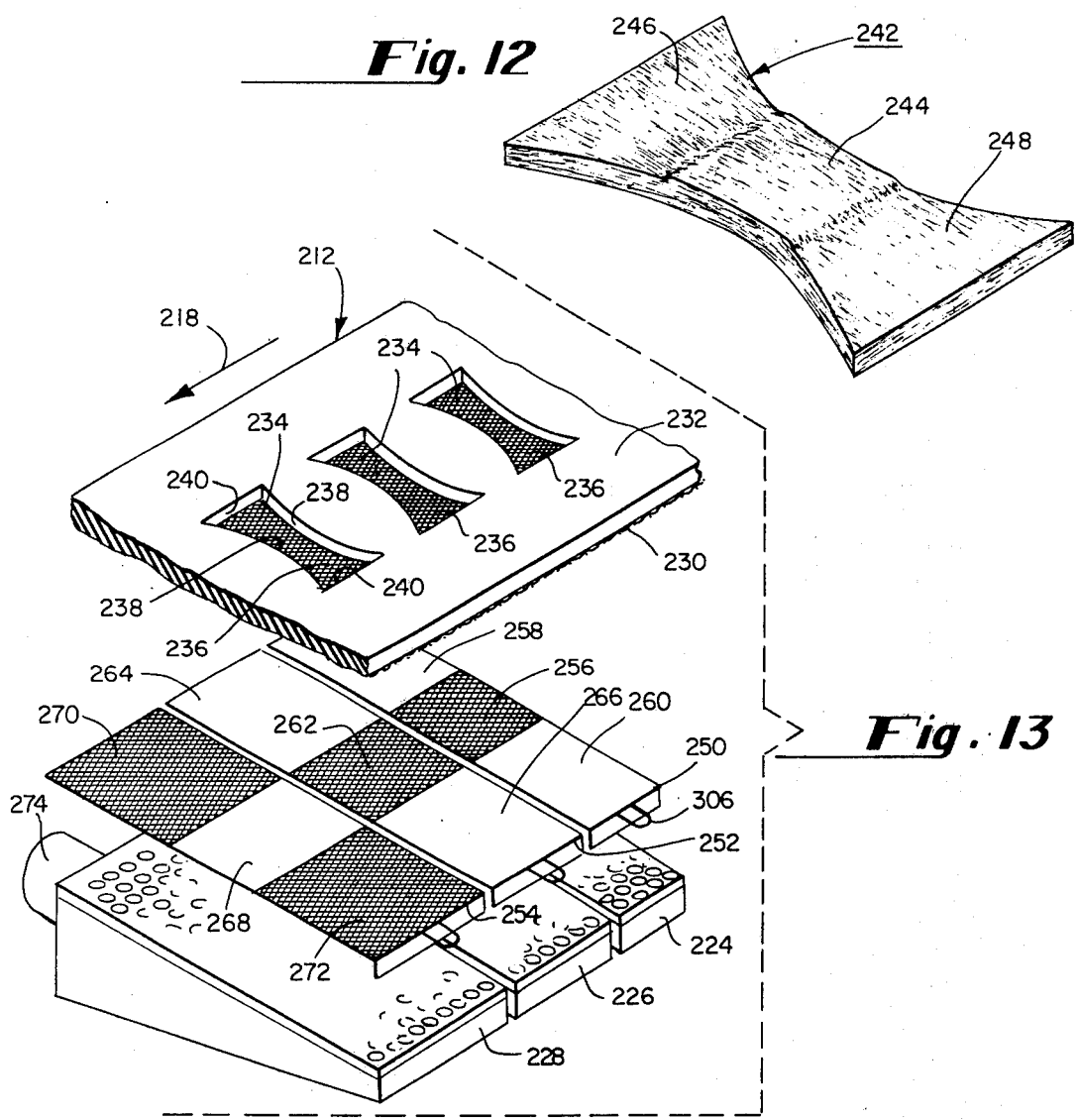
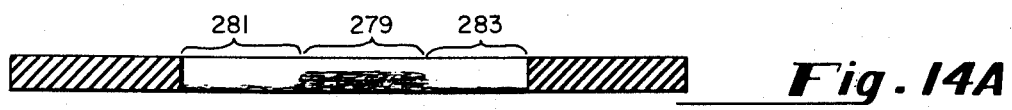
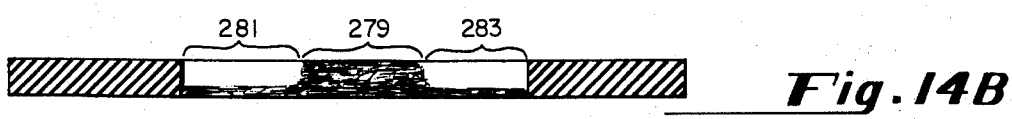

METHOD FOR FORMING FIBROUS PADS

RELATED APPLICATIONS

This application is a division of U.S. pat. application Ser. No. 237,963, filed Mar. 24, 1972, now U.S. Pat. No. 3,846,871 entitled Apparatus for Forming Fibrous Pads, which in turn is a continuation-in-part of Ser. No. 67,862, filed Aug. 28, 1970, now abandoned.

BACKGROUND OF THE INVENTION

1. Field of the Invention

This invention relates to apparatus and methods for forming fibrous pads, and more specifically to apparatus and methods for forming discrete pads of a desired shape and profile.

Reference to "shape" throughout this application, including the claims, in describing the structure of a fibrous pad, refers to the configuration of the pad in plan view.

Reference to "profile", as used throughout this application, including the claims, in describing the structure of a fibrous pad, refers to a varying weight distribution of fibers in the pad such that the pad has a predetermined region with a weight of fibers per unit area therein which is different than the weight of fibers per unit area in at least one other predetermined region of the pad.

2. Description of the Prior Art

Many sanitary products, such as disposable diapers, sanitary napkins and the like, utilize an absorbent fibrous pad as one component thereof. This pad, in many instances, must have a specific shape which can be reproduced in an economical mass production operation. One prior art apparatus for producing discrete fibrous pads is disclosed in U.S. Pat. No. 2,940,133, issued to Heritage. This patent discloses an apparatus employing a drumtype condenser upon which fibrous pads are formed. The condenser is masked to define air-permeable surfaces defining the shape of fibrous pads to be formed. The air-permeable surfaces are separated by air-impermeable surfaces which are disposed substantially in the same plane as the air-permeable surfaces. It is difficult to form fibrous pads having the specific shape of the air-permeable surfaces in a repeatable fashion by utilizing an apparatus such as is disclosed in the Heritage patent. One major reason for this difficulty is that air-suspended fibers which are initially directed toward the masked, air-impermeable surfaces of the condenser are deflected to the perimeter of the unmasked, air-permeable surfaces by a vacuum applied from within said condenser. The air suspension of fibers impinges on the boundaries of the air-permeable surfaces at various angles to cause random deposits of fibers adjacent the perimeters of the unmasked surfaces of the condenser. These random deposits cause distortions in the shape of the formed fibrous pads.

Other prior-art apparatus for forming fibrous pads have employed drum-type condensers with three-dimensional pad-receiving compartments extending inwardly from a peripheral surface thereof. Such priorart apparatus are exemplified in U.S. Pat. No. 3,518,726, issued to Banks; and in U.S. Pat. No. 1,950,765, issued to Winter. These drum-type condensers, as well as the drum-type condenser disclosed in the Heritage patent, have several deficiencies. In order to obtain controlled pad formation, an air suspension of fibers should be directed either tangent or perpendicular to the forming run of a pad-formation assembly. When the air suspension of fibers is directed tangent to the forming run a cloud of air-suspended fibers is established above the forming run. This cloud can be directed in a controlled manner into the pad-receiving compartments by a partial vacuum created through a vacuum source disposed below said forming run. When the air suspension of fibers is directed perpendicular to the forming run the fibers also are easily diverted into the pad-receiving compartments in a controlled manner to establish controlled pad formation. When the air suspension of fibers is directed toward the pad-formation assembly at orientations other than tangent or perpendicular to the forming run, uncontrolled, non-uniform fiber distribution occurs at either the trailing or leading edge of each compartment, depending upon the specific orientation of the stream of air suspended fibers relative to the compartments. Theoretically, no complete pad-receiving compartment or discrete pad-receiving area of a drum-type condenser is oriented either perpendicular or tangent to a stream of air suspended fibers at any given time during the pad forming operation. Practically, only about 90° of the periphery of a drum-type condenser at any given time during the pad forming operation is so oriented with respect to a stream of air suspended fibers that adequate control of pad formation can be achieved.

Apparatus employing drum-type condensers are speed limited by the fact that a major portion of the condenser surface, at any given time, is not properly oriented to be utilized in forming shaped pads in a controllable manner. To increase the pad output in apparatus employing a drum-type condenser, the condenser must be operated at extremely high speeds, and/or the drum-type condenser must have an extremely large diameter such that 90° of the periphery of the condenser represents a large surface upon which several discrete pads can be formed. Operating a drum-type condenser at extremely high speeds will cause the fibers to be thrown off the condenser by centrifugal force, and thereby cause uncontrollable variations in the formed pads. Large drum-type condensers are cumbersome to handle, and difficult to assemble on a mounting axle. When such a condenser has to be changed; for example, when a fibrous pad having a different shape is to be formed; heavy equipment, such as a crane, normally must be employed. If the drum-type condenser is made in segments, changing the condenser will not require the use of heavy equipment; however, assemblying a segmented condenser is time consuming, and involves the additional problem of establishing effective seals between the segments.

In the Banks patent (3,518,726) each pad-receiving compartment has a varying thickness in a circumferential direction resulting from the formation of each compartment by arcuate side plates and a substantially flat perforated bottom plate. In this construction the pad-receiving compartments are thicker in the center than at opposed ends, and the pads formed in such compartments will assume the profile of the compartments. The banks+ drum-type condenser lacks versatility since a pad having only one specific profile can be formed therein, i.e. a pad having a greater weight of fibers per unit area in the center region than in adjacent end regions. To form fibrous pads with a different profile, the drum-type condenser must be replaced by one having surfaces therein defining a compartment having a profile corresponding to that of the pad to be formed. This change of condensers can be a cumbersome, difficult to achieve task, as explained earlier in this application. Furthermore, the specific configuration of surfaces defining compartments of different profiles may be fairly intricate and difficult to form in drum-type condensers.

In many applications it is desirable to form a fibrous pad which is profiled in the cross-machine-direction, i.e. a fibrous pad wherein different predetermined regions having different weights of fibers per unit area therein are spaced from each other in the cross-machine-direction. The apparatus disclosed in Banks is designed only for forming fibrous pads which are profiled in the machine-direction. Banks does not suggest an apparatus for forming fibrous pads profiled in the cross-machine-direction.

In the Banks apparatus, the pads can be somewhat easily removed from the drum-type condenser because of the tab connection between adjacent pads. To further explain, if one of the pads is removed from a compartment it will tend to lift adjacent pads out of their respective compartments as a result of the force transmitted to these adjacent pads through the tab connections. However, when fibrous pads are formed as discrete, separate members, a problem exists in removing such pads from three-dimensional compartments in drum-type condensers. In order to remove discrete pads from the compartments, the vacuum applied through the lower surface of the compartments must be cut off. When the vacuum is cut off air is permitted to become entrapped between fibers in the pads to expand the pads into engagement with the peripheral side walls defining the compartments. This expansion of fibers creates frictional drag against the side walls, and prevents easy removal of the pads from the compartments.

Apparatus employing a pad-formation assembly having a substantially linear forming run, and allegedly operable to form pads of a particular shape in a repeatable fashion is disclosed in U.S. Pat. No. 2,949,646. The apparatus disclosed in this patent utilizes a three-dimensional masking frame assembly having individual masking elements with openings therein which define the shape of the pads to be formed. A conveyor system movable in synchronism with the masking frame assembly is disposed beneath the three-dimensional masking frame assembly, and this conveyor system is foraminous along its entire extent, i.e. the conveyor system is not provided with masked, air-impermeable regions and unmasked, air-permeable regions. Each masking element has a pad-defining opening, and the regions outside of this opening are foraminous. The fibers carried in an air stream are directed toward the conveyor and masking elements from above the masking elements. The fibers directed into the openings of the masking element deposit on the conveyor to form pads generally having the shape of the opening. The remaining fibers are deposited on the foraminous regions of the masking elements, and therefore are not utilized to form pads. The fibers deposited on the foraminous regions of the masking elements should be recycled back into the process to achieve optimum utilization of fibers. Equipment for recycling the fibers increases the complexity and cost of the apparatus.

The apparatus disclosed in U.S. Pat. No. 2,949,646, does not utilize a vacuum source to hold the formed pads on the conveyor at the point of separation between the conveyor and the three-dimensional masking frame assembly. Therefore, some distortion or destruction of the pads may occur because of a stronger affinity of the fibers for the masking frame assembly, than for the underlying conveyor.

Air directed through regions of the conveyor underlying the foraminous portions of the masking elements may cause fibers to displace from the region defined by openings in the masking elements to become trapped between the conveyor and the foraminous portions of the masking elements. The displacement of fibers occurs because the regions of the conveyor underlying the foraminous portions of the masking elements are not masked to the passage of air. These trapped fibers can adhere to the pads which are formed and thereby cause distortions in the finished pad. This prevents the repeatable reproduction of fibrous pads of a required shape.

U.S. Pat. No. 3,501,813, issued to Lee et al, discloses an apparatus for making a continuous, profiled fibrous web having a longitudinally extending medial regions with a greater weight of fibers per unit area therein than longitudinally extending flanking side regions. The Lee et al apparatus requires the use of baffles to engage an air-suspension of fibers within a conveying duct to deflect the fibers into overlying relationship with a medial region of a foraminous conveyor upon which the web is to be formed. This deflection increases the volumetric flow rate of the deflected portion of the air suspension of fibers. Lee et al allegedly compensates for this increased flow rate by regulating valve openings in a vacuum box disposed behind the foraminous conveyor to permit the region of the vacuum box underlying the medial region of the foraminous conveyor to accommodate the increased air flow.

The Lee et al apparatus has several deficiencies. First, the use of baffles to deflect the air suspension of fibers results in a more complex apparatus than one in which deflecting baffles are not used. Second, when it is desired to form continuous fibrous webs with different profiles, the baffles must be rearranged within the duct through which the air suspension of fibers is directed. This rearrangement of baffles can be a difficult and a time consuming task. In some instances the baffles may not be relocatable to a required position to permit formation of a continuous fibrous web having a required profile. Therefore, the Lee et al apparatus lacks the desired degree of versatility to easily permit its use for forming continuous fibrous webs having many different profiles.

U.S. Pat. No. 3,598,680, issued to Lee, discloses an apparatus for forming continuous fibrous webs having a longitudinally extending medial region with a greater weight of fibers per unit area therein than in flanking side regions. This apparatus is described as an improvement over the Lee et al apparatus discussed above, and employs separate fiberizing devices, and separate formation chambers to form the continuous, profiled fibrous web. This apparatus lacks versatility in permitting the formation of continuous fibrous webs having many different types of profiles. In order to vary the profile of a continuous fibrous web, extensive modifications to the equipment are required. For example, the formation chambers at various locations would have to be reoriented to overlie different sections of the foraminous conveyor upon which the web is to be formed. This requires considerable machine reconstruction, and therefore is highly undesirable.

The apparatus and method disclosed in both the Lee et al and the Lee patents relate to the formation of continuous profiled webs, and in no way suggest a method and/or apparatus for forming discrete fibrous pads having a desired shape and profile, which can be varied in a simple and reliable manner.

The method of continuous web formation disclosed in both the Lee et al and Lee patents requires the formation of separate fibrous strips which overlap each other in certain regions to define a thickened region, i.e. a region having a greater weight of fibers per unit area therein than in non-overlapped regions of the strips. Stating this another way, the method disclosed in both the Lee et al and the Lee patent requires the formation of at least a portion of a thickened region simultaneously with the formation of a different region having a lesser weight of fibers per unit area therein than in the thickened region. Therefore, certain stages of the web forming operation disclosed in both the Lee et al patent and the Lee patent depend upon the masking effect, i.e. resistance effect, of a portion of the web formed in a specific predetermined region during a previous stage of the web forming operation. In a later stage of the web forming operation the fibers will be deposited initially in an unformed region of the web since the resistance to air flow in such unformed region is considerably less than the resistance through a partially formed region of the web. As the web forming operation proceeds, the resistance to air flow increases in what was the unformed region of the web as a result of the build up of fibers in said region, and the air suspension of fibers tends to divide to deposit fibers in different predetermined regions. This division of the air suspension of fibers is not controllable, since the changing resistance characteristics resulting from the build up of fibers in different predetermined regions cannot be determined or controlled easily during the web forming operation. Furthermore, as the weight of fibers per unit area in one predetermined region approaches the weight of fibers in a different predetermined region a self-leveling effect occurs which tends to destroy the profile of the web and thereby create an unprofiled web having a substantially uniform weight of fibers per unit area throughout. Therefore, the methods of web formation disclosed in both the Lee and the Lee et al patents preclude the controlled formation of profiled pads in which the weight of fibers in different predetermined regions are different but quite close to each other, and makes difficult to varying degrees all profiles except those in which the differences in the weight of fibers per unit area in different predetermined regions are extreme.

SUMMARY OF THE INVENTION

Apparatus of this invention for forming fibrous pads include a pad-formation assembly having spaced, three-dimensional pad-receiving compartments; adjacent compartments being separated by air-impermeable regions. Each compartment has the shape of a fibrous pad to be formed therein and is defined by a lower air-permeable surface and air-impermeable sidewalls extending outwardly from the air-permeable surface and disposed contiguous to said air-permeable surface. The sidewalls provide positive control for the shape of fibrous pads to be formed, and thereby eliminate distortions at the perimeter of the formed pads. Sidewall sections defining each compartment are movable relative to the lower air-permeable surface to aid in releasing formed pads from said compartments.

The apparatus of this invention includes drive means for moving a substantially linear forming run of the pad-formation assembly through a pad forming region. By employing a substantially linear forming run the apparatus of this invention can be run at high speeds without encountering the adverse effects of centrifugal force which are encountered in apparatus employing drum-type condensers.

The pad forming region includes a fiberizing means for individualizing fibers from a feed matt and for forming an air suspension of said individualized fibers. The pad forming region further includes vacuum means disposed behind the forming run for creating a partial vacuum to direct said air suspension of fibers into the pad-receiving compartments whereat the air of siad suspension is pulled through the lower surface, and the fibers of said suspension are deposited within the confines of said compartments to form fibrous pads of a desired shape. Since the pad-receiving compartments in the pad-formation assembly of this invention are separated from each other by air-impermeable regions, the vacuum means disposed behind the forming run is effective to pull the air-suspension of fibers only into the pad-receiving compartments, and not into the air-impermeable regions. Therefore, fibers directed into the pad-receiving compartments will not tend to be displaced laterally to cause distortions in the shape of the completed fibrous pads. Furthermore, the quantity of fibers which does deposit on the air-impermeable regions of the pad-formation assembly is not so great as to require fiber recycling equipment.

In a first specific embodiment of the apparatus of this invention the pad-formation assembly includes an endlessly mounted masking frame assembly and an endlessly mounted masked conveyor. The masking frame assembly includes frame members having side surfaces defining spaced openings which have the general shape of fibrous pads to be formed, said side surfaces defining the side walls of the pad-receiving compartments. The masked conveyor includes spaced, air-permeable surfaces having the general configuration, or shape, of a fibrous pad to be formed. The air-permeable surfaces define the lower surface of the pad-receiving compartments, and are separated from each other by air-impermeable regions. The masking frame assembly is moved in synchronism with the masked conveyor to define a linearly extending pad forming run which is directed through the pad-forming region with the spaced openings defined by the side surfaces of the frame members disposed in overlying relationship with the air-permeable surfaces of the masked conveyor. A sealing means is provided on the bottom surface of the frame members for engaging the conveyor as the conveyor and masking frame assembly pass through the pad-forming region to insure that fibers do not become trapped between the frame members of the masking frame assembly and the masked conveyor.

The side surfaces of the frame members which define the sidewall sections of the pad-receiving compartments are moved relative to the lower, air-permeable surface of the masked conveyor by separating the masking frame assembly from the masked conveyor at the downstream end of the pad forming run. In this manner, the formed pads are retained only on a substantially flat surface of the masked conveyor and can be transferred easily to a take-off conveyor positioned downstream of the pad-forming region of the apparatus.

A vacuum means is disposed behind the masked conveyor for continuously pulling a partial vacuum through the air-permeable surfaces of the masked conveyor at the downstream end of the pad-forming region whereat the masking frame assembly is separated from the masked conveyor. The application of a vacuum during separation of the masking frame assembly from the masked conveyor assures that the pad is retained on the conveyor, as opposed to the masking frame assembly, and assures that this retention occurs without distorting the formed fibrous pads.

A unique masking frame assembly and a drive and connection system for said assembly forms a part of this invention. The masking frame assembly is comprised of frame members which are removably secured to support members. The frame members can be changed to define openings of different shapes in the event that fibrous pads of different shapes are to be formed. The support members are interconnected in a desired spaced relationship by a plurality of links, and adjacent links are interconnected by pins extending from a chain into aligned openings of said adjacent links. The links are interconnected to permit relative rotational and linear movement between links to permit a change in cord length of the drive and connection system as said system turns about spaced rolls at the upstream and downstream end of the linear pad-forming run.

A second preferred embodiment of an apparatus of this invention has a pad-formation assembly provided by a relatively thick, i.e. ¼ inch to about 1 inch, flexible substrate directly adhered to an endless conveyor. The flexible substrate replaces the masking frame assembly employed in the first embodiment of this invention, and has sections removed therefrom to expose air-permeable surfaces of the conveyor which define the lower, air-permeable surfaces of the pad-receiving compartments. Surfaces of the flexible substrate which are formed by the removal of sections therefrom define the sidewalls of the pad-receiving compartments, and adjacent compartments are separated from each other by air-impermeable regions. The air-impermeable regions can be defined by the flexible substrate, or in the event the flexible substrate is air-permeable, the surface of the conveyor underlying the flexible substrate can be coated with a suitable air-impermeable material, such as neoprene. The pad-formation assembly is mounted in an endless fashion about spaced rolls to define a substantially linear forming run to overcome the deficiencies of prior-art apparatus employing drumtype condensers. A vacuum means is disposed below the pad-forming run for directing the air-suspension of fibers into the padreceiving compartments in the same manner as in the first embodiment of this invention.

The pad-formation assembly includes a linear pad-transfer run opposed to the linear pad-forming run, and formed pads are transferred from this transfer run to a second, pad-receiving conveyor. The flexible substrate expands as the pad-transfer run turns, at its downstream end, about one of the spaced rolls to enter the upstream end of the pad-forming run. This expansion causes sidewall sections defining the pad-receiving compartments to move relative to each other and to the lower surfaces of said pad-receiving compartments to aid in releasing the formed fibrous pads from the compartments of the transfer run to permit relatively easy transfer of the formed pads to the pad-receiving conveyor. Applicant has discovered that this movement of the sidewall sections is extremely desirable in enhancing pad removal from the pad-formation assembly.

This invention further relates to apparatus and method for forming discrete, shaped, profile pads. Such apparatus is substantially identical to the first and second embodiments of this invention, and further includes profiling masking means disposed between the vacuum means and the pad-forming run of the padformation assembly. The profiling masking means prevents the establishment of a partial vacuum through different predetermined sections of the pad-receiving compartments during different stages of pad formation to thereby establish a different "effective volumetric air flow" through the different predetermined sections. In this manner a weight of fibers per unit area is deposited in one predetermined section which is different from the weight of fibers per unit area which is deposited in a second predetermined section.

Reference to "effective volumetric air flow" throughout this application, including the claims, refers to the total volumetric flow of air through a predetermined section of each pad-receiving compartment to provide a desired weight of fibers per unit area in said predetermined section. A different effective volumetric air flow can be established through different predetermined sections of the pad-receiving compartments by any one of the following means:

1. establishing the same volumetric demand for air per unit time through a vacuum means for different lengths of time through different predetermined sections of the padreceiving compartments; or 2. establishing a different volumetric demand for air per unit time through a vacuum means for the same or different lengths of time through different predetermined sections of the pad-receiving compartments.

A further aspect of this invention relates to a unique method for forming discrete, profiled fibrous pads wherein the weight of fibers per unit area in different predetermined regions can be established to be different than, but quite close to each other. Applicant has discovered that the formation of a profiled fibrous pad cannot be controlled within close tolerances by establishing a different amount of open area through which air can be drawn by a vacuum box through different predetermined regions underlying the different predetermined sections of the pad-receiving compartment in which different weights of fibers per unit area are to be deposited. In the prior art methods for forming profiled webs, a different amount of open area through which air can be directed by a source of a vacuum has been established by varying the concentration of open area in a foraminous member disposed over the sources of vacuum and also by regulating valve openings associated with the source of vacuum.

Applicant has discovered that, except for extremely low basis weight fiber deposits, resistance to air flow through a padreceiving compartment is greatly influenced by the basis weight of a partially formed web deposited in said compartment during the pad forming operation; and that the effect on fiber distribution which is achieved by varying the amount of open area through which air can be directed by a vacuum source is not as significant as the effect of a partially formed fibrous web. Based on this discovery, applicant recognized that the only effective means for establishing different weights of fiber per unit area in different predetermined regions of a fibrous pad, while maintaining close tolerances, is to completely form each predetermined region with a specific weight of fibers per unit area therein substantially independently of the formation of every other predetermined region having a different weight of fibers per unit area therein. Applicant's unique method of this invention includes completely masking off a source of vacuum to all sections of each pad-receiving compartment except the section in which a region of a fibrous pad having a particular weight of fibers per unit area is to be formed. After this region has been completely formed, the vacuum source underlying the formed region is completely masked to the passage of air, and a second section of each pad-receiving compartment is exposed to vacuum to form a predetermined region of the pad having a different weight of fibers per unit area therein. The weight of fibers per unit area deposited within a predetermined section of each compartment can be controlled by selecting the time of exposure of said predetermined section to a vacuum and controlling the volumetric air demand per unit time of the source of vacuum. Since, at any given time, a partial vacuum only is established through the sections of each pad-receiving compartment which are to receive the same weight of fibers per unit area therein, the weight of fibers per unit area deposited in each predetermined region of the fibrous pad can be controlled accurately by controlling the volumetric air demand of the vacuum source and the predetermined time of exposure to said partial vacuum of each predetermined section of each compartment.

The volumetric air demand of the vacuum source and the time of exposure to vacuum can be set within wide limits, depending upon the weight of fibers per unit area which is to be deposited in a predetermined section of the pad-receiving compartments. However, the volumetric air demand per unit time of the vacuum source should not be so great as to cause a fiber layer to excessively felt or compact to a level which will prevent air from being drawn through said fiber layer before complete formation thereof.

It is an object of this invention to form shaped fibrous pads in a simple, reliable and repeatable fashion.

It is a further object of this invention to form shaped fibrous pads in which the shape easily can be varied for different end uses of said fibrous pad.

It is a further object of this invention to form shaped pads which easily are transferable from pad-forming equipment to subsequent converting equipment.

It is a further object of this invention to form shaped, profiled fibrous pads in a simple, reliable and repeatable fashion.

It is a further object of this invention to form shaped, profiled fibrous pads in which close tolerances in the weight of fibers per unit area can be maintained in a repeatable fashion in predetermined regions of said fibrous pad.

Other objects and advantages of this invention will become apparent upon referring to the detailed description which follows taken in conjunction with the drawings.

BRIEF DESCRIPTION OF THE DRAWINGS

FIG. 9 is a schematic view of an apparatus according to a second preferred embodiment of this invention;

FIG. 10 is an enlarged view of the blocked portion of FIG. 9 identified as "10";

FIG. 11 is an enlarged view of the blocked portion of FIG. 9 identified as "11";

FIG. 12 is an isometric view of a fibrous pad which can be manufactured by the apparatus of FIG. 9;

FIG. 13 is an exploded isometric view of portions of the apparatus shown in FIG. 9, and utilized for forming the fibrous pad shown in FIG. 12;

FIGS. 14A, 14B and 14C show the cross sectional profile of the fibrous pad shown in FIG. 12 during sequential stages of formation according to the preferred method of this invention;

DESCRIPTION OF THE PREFERRED EMBODIMENTS

Figure 1:
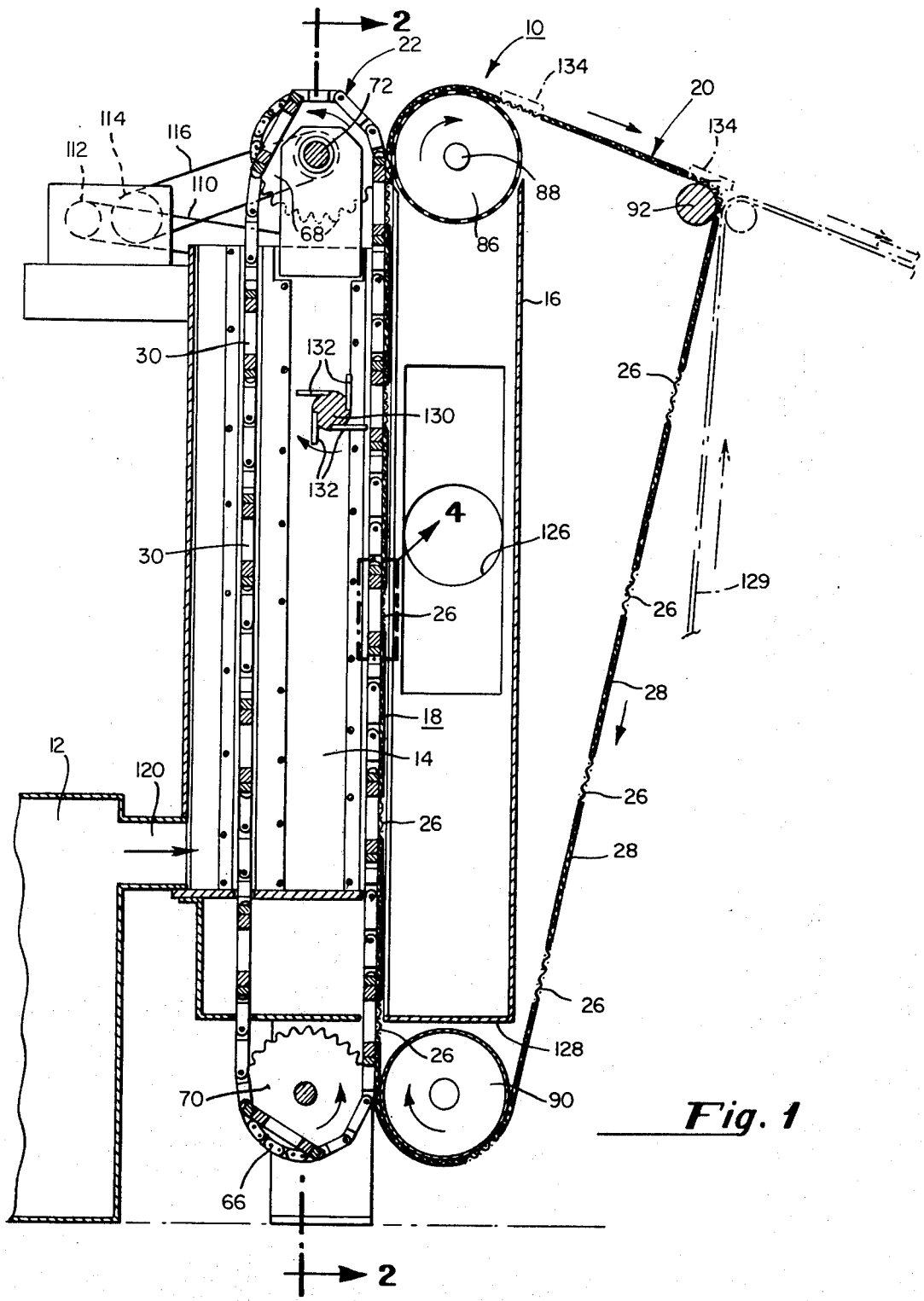
FIG. 1 is a sectional side elevation of an apparatus of this invention taken along line 1-1 of FIG. 2.

Referring to FIG. 1, a first embodiment of a pad forming apparatus 10 of this invention comprises a fiberizing means 12 for separating fibers of a pulp lap and for forming an air suspension of said fibers within a pad forming chamber 14. A vacuum box 16 is disposed behind a pad-forming run 18 of a masked conveyor 20 which, along with a masking frame assembly 22 forms a unique pad-formation assembly of this invention. The vacuum box 16 is operative to pull airborne fibers which are in chamber 14 onto the masked conveyor 20 whereby fibrous pads (e.g. 134, FIG. 7) are formed on the conveyor and carried thereby to other converting equipment.

The unique pad-formation assembly of this invention is most clearly illustrated in FIGS. 1-5, and, as stated above, includes the masked conveyor 20 and the masking frame assembly 22. The masked conveyor 20 has air-impermeable regions 28. The air-impermeable regions generally define a configuration, or shape of the air-permeable surfaces 26 corresponding to the configuration, or shape of fibrous pads which are to be formed. The masked conveyor 20 is formed from a mesh screen of fiberglass in which the air-impermeable regions 28 are formed by a semi-conductive Teflon coating which is substantially flush with the surfaces of the mesh screen. The Teflon coating dissipates static charges which build up on the fibers during the fiberizing operation. Coatings other than Teflon can be utilized; however, it is preferred, but not required, that such coatings be capable of dissipating static charges on the fibers.

Figure 5:
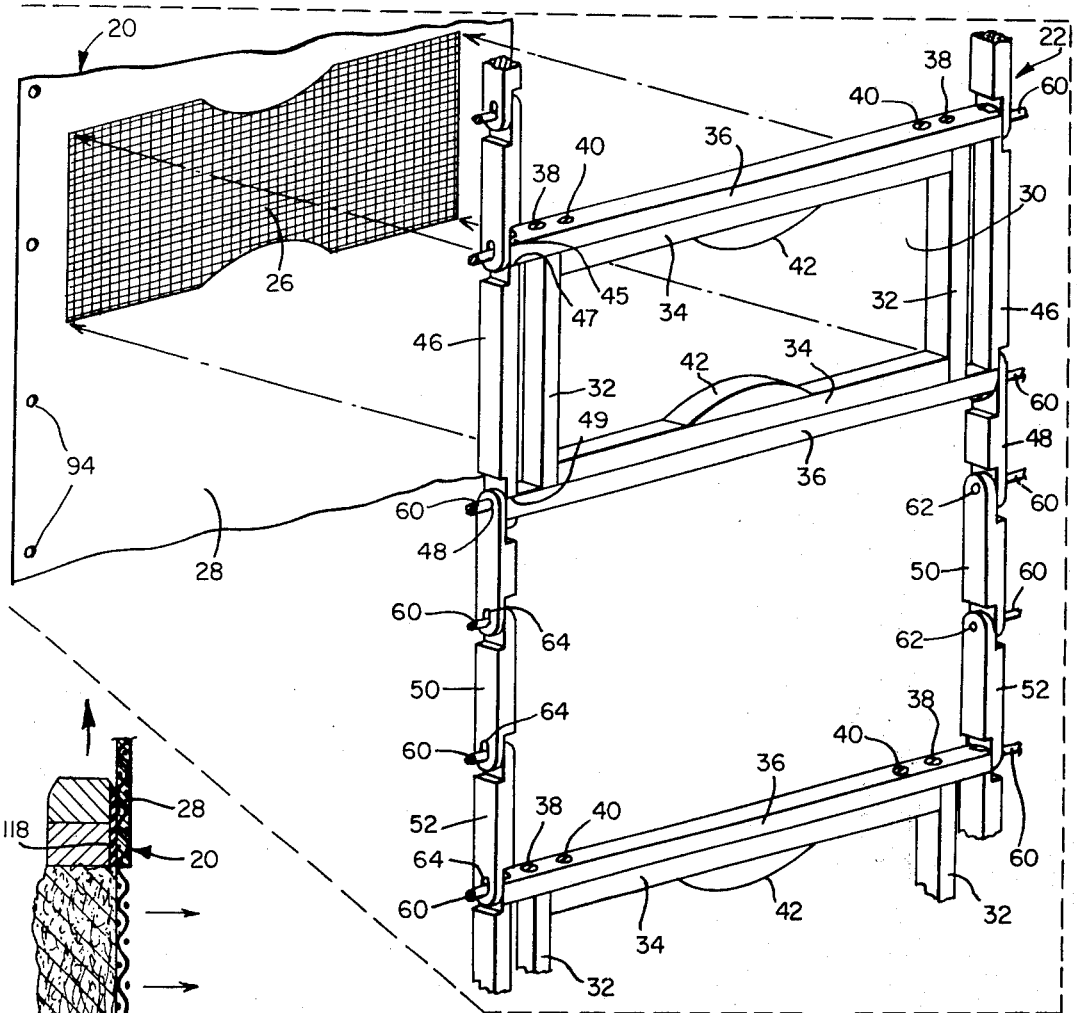
FIG. 5 is an exploded isometric view of a pad-formation assembly, including a masking frame assembly and a masked conveyor, employed in an apparatus of this invention.

Referring to FIG. 5, the masking frame assembly 22 is comprised of a plurality of frame members, and the frame members are disposed in sets such that side surfaces of the frame members in each set define an opening 30 having the shaping of a pad to be formed. Each set of frame member is comprised of vertical frame members 32 and transversely-extending frame members 34. The vertical frame members 32 and transversely extending frame members 34 are connected to vertically spaced, horizontal support members 36 by screws 38 and 40, respectively. Each transversely-extending frame member 34 has an arcuate protuberance 42 which is either formed integrally therewith, or is removably connected thereto by suitable fastening means (not shown).

The vertically spaced, horizontal support members 36 of each set of frame members are bifurcated to define spaced legs 45 which straddle the upper and lower ends, respectively, of a frame support and positioning link 46 (FIG. 5). The lower surface of each leg 45 is supported on shoulders 47, 49 at the upper and lower ends, respectively, of each link 46.

Figure 2:
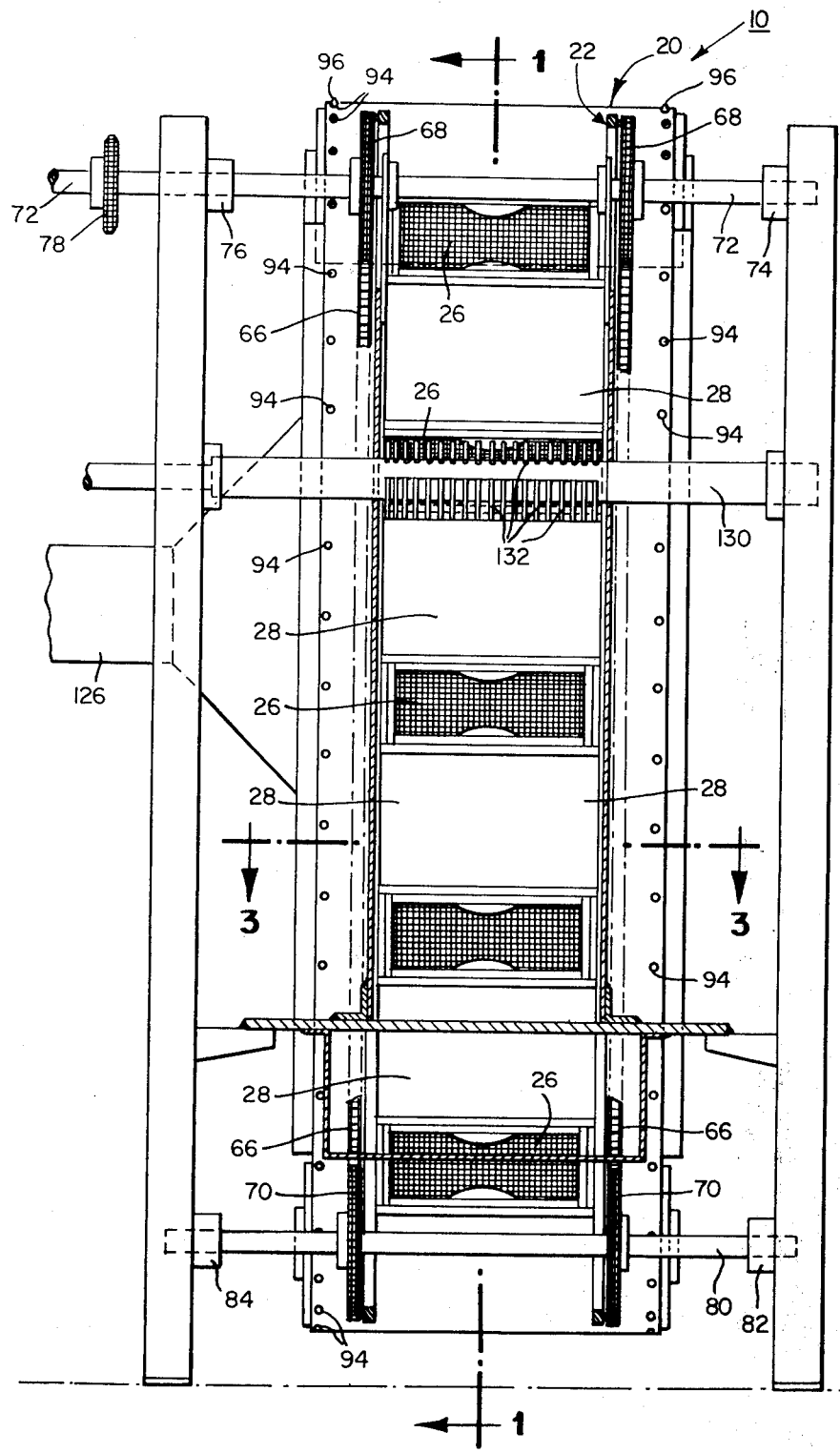
FIG. 2 is a sectional front elevation view of an apparatus of this invention taken along line 2-2 of FIG. 1.
Figure 3:
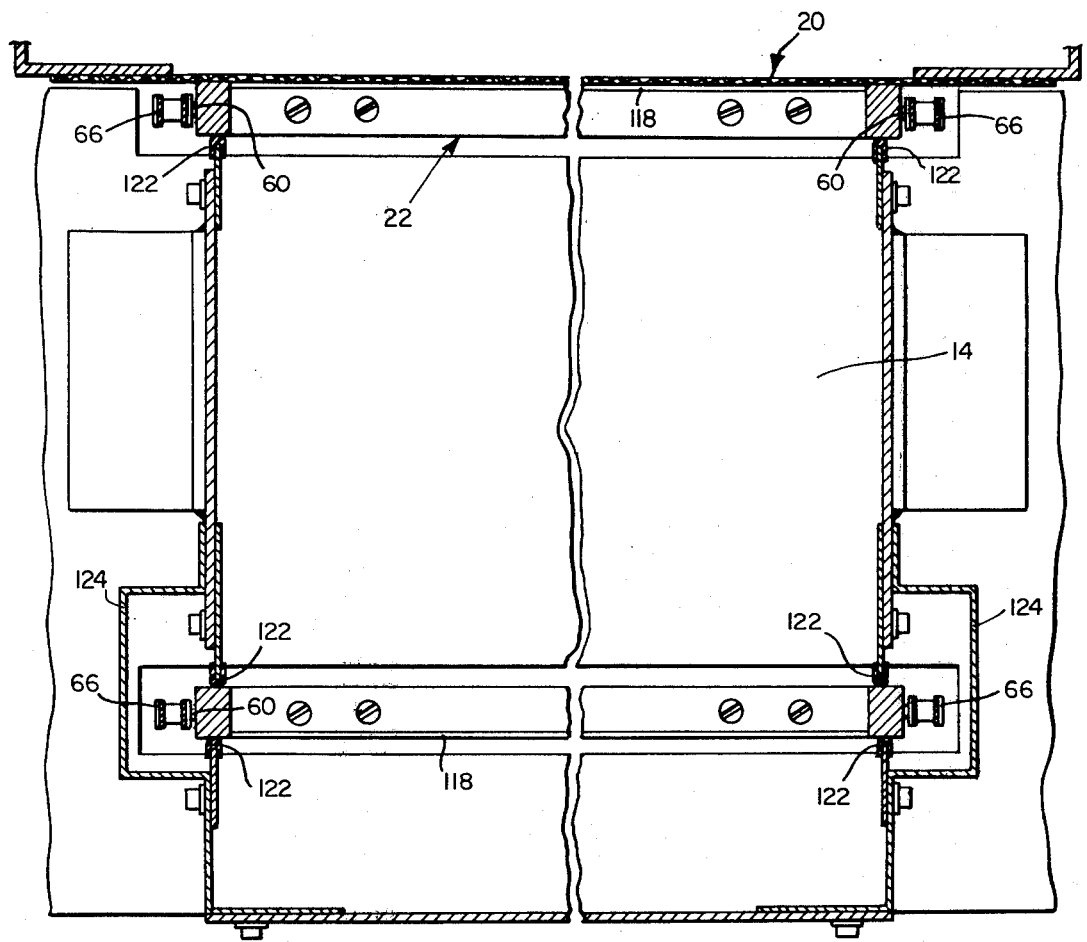
FIG. 3 is a sectional view of an apparatus of this invention taken along line 3-3 of FIG. 2.

In the preferred embodiment of the invention, adjacent sets of frame members are interconnected in spaced relationship to each other by a series of frame support and positioning links 46-48-50-52. As can readily be observed in FIG. 5, the links are interconnected to each other by pins 60 which extend through aligned openings 62 and 64 at the upper and lower ends of each link. As can be seen in FIG. 3, the pins 60 which interconnect the various links together are connected to, and extend from driven chains 66. Each driven chain 66 is trained in an endless fashion about a driven sprocket wheel 68 and a freely rotatable idler sprocket wheel 70 (FIGS. 1 and 2). The opening 64 in each link is elongate to permit relative linear movement between respective links. The relative linear movement between links is required to permit a change in cord length as the links reverse direction about the sprocket wheels 68 and 70.

The driven sprocket wheels 68 are fixedly secured to a driven shaft 72 which is mounted for rotation in bearing blocks 74–76 (FIG. 2). The end of the driven shaft 72 extending through the bearing block 76 has a sprocket wheel 78 fixedly secured thereto (FIG. 2 and FIG. 8), and it is through sprocket wheel 78 that the shaft 72 is driven by a drive system to be described later. The idler sprocket wheels 70 are fixedly secured to an idler shaft 80 mounted for rotation in bearing blocks 82–84 (FIG. 2).

The masked conveyor 20 is mounted in an endless fashion about a roll 86 fixed to a driven shaft 88 (FIG. 1 and 8), and about a pair of idler rolls 90–92 (FIG. 1). The masked conveyor 20 is provided with a row of openings 94 extending along each marginal edge thereof for engagement with upwardly-extending pins 96 which are connected to the driven roll 86 (FIG. 2). The number and arrangement of sprocket wheels and rolls over which the masked conveyor 20 and masking frame assembly 22 are trained, and the details of the drive are not critical to this invention and may be varied.

Figure 8:
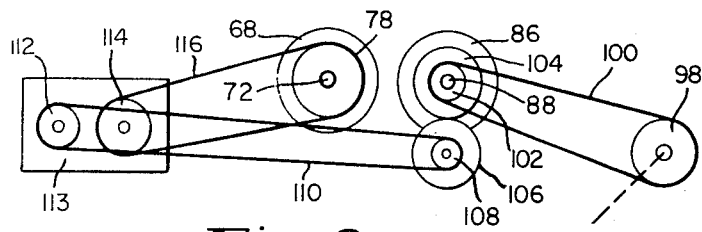
FIG. 8 is a schematic view of the drive means for moving the masked conveyor and masking frame assembly in synchronization.

Referring now to FIG. 8, the details of operation of the drive control mechanism for synchronizing the movement of the masked conveyor 20 and the masking frame assembly 22 will be described. A power source, such as a motor (not shown), drives a sprocket wheel 98. A chain 100 is trained about the sprocket wheel 98 and a sprocket wheel 102 which is fixedly connected to the driven shaft 88 to thereby rotate said shaft. As described above, the driven roll 86 for rotating the masked conveyor 20 is also fixedly connected to the shaft 88; therefore, rotation of shaft 88 drives the roll 86 to drive the masked conveyor 20. A gear 104 is also fixedly connected to the shaft 88 and is driven by rotation of said shaft to rotate a gear 106 which is in meshing engagement therewith. A sprocket wheel 108 is fixed with the gear 106 to rotate therewith, and a chain 110 is trained about the sprocket wheel 108 and a sprocket wheel 112 to thereby rotate said sprocket wheel 112. The sprocket wheel 112 feeds into a differential gear box 113 to drive an output sprocket wheel 114 at a rotational velocity which is synchronized with the input velocity of the sprocket wheel 112.

The output sprocket wheel 114 drives a chain 116 which is connected to sprocket wheel 78 (FIG. 2 and 8). The sprocket wheel 78 is fixedly connected to the driven shaft 72 (FIG. 2 and 8) to thereby drive the shaft 72 and the driven sprocket wheels 68 connected thereto. The differential gear box 113 permits phase adjustments to be made between shaft 72 and shaft 88 when the air permeable surfaces 26 of masked conveyor 20 move out of alignment with the openings 30 defined by the frame members of the masking frame assembly 22. Some slight misalignment may occur after a period of operation of the apparatus as a result of tolerance variations in the various components of the pad-formation assembly 24. By energizing the differential gear box 113 when a misalignment occurs, the pad-formation assembly 24 is controlled to insure that the openings 30 defined by the frame members 24, 26 will remain in overlying relationship with the porous, air permeable surfaces 26 (FIG. 2) as the masked conveyor 20 and masking frame assembly 22 pass through the pad forming chamber 14 (FIG. 1 and 3) of the apparatus 10.

The masked conveyor 20 and masking frame assembly 22 cooperate to define three-dimensional pad-receiving compartments to eliminate undesirable peripheral edge effects in the formed pads which are otherwise encountered when pads are formed on substantially planar surfaces without sidewall boundaries. Furthermore, the three-dimensional pad-receiving compartments move along a substantially linear forming run 18 along the pad forming chamber 14 to eliminate the problems encountered with the use of drum-type condensers, all as has been set forth earlier in this application.

Figure 4:
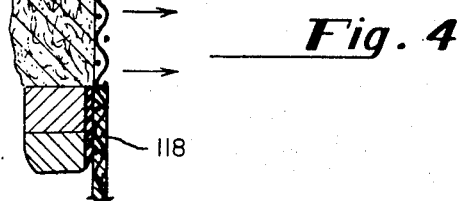
FIG. 4 is an enlarged view of the blocked portion of the apparatus shown in FIG. 1.

As shown in FIGS. 3 and 4, suitable elastic seals 118 are integrally connected to the lower surfaces of the vertical and horizontal frame members 32, 34 respectively. The seals 118 engage with the surface of the masked conveyor 20 to provide intimate sealing engagement between the frame members of the masking frame assembly and masked conveyor. This sealing arrangement has been found highly desirable in preventing fibers from becoming entrapped between the frame members of the masking frame assembly and masked conveyor. If fibers became entrapped, they cause undesirable distortions in the configuration, or shape of the finished pad.

Referring again to FIG. 1, the fiberizing means 12 is connected to the pad forming chamber 14 through a conduit 120. Any suitable fiberizing means, such as a Joa fiberizer, Hammermill, etc., can be utilized in the apparatus 10 of this invention. In the preferred embodiment of the invention, pulp lap is fed into a Joa fiberizer having a rotating lickerin roll to separate or individualize fibers from said lap, and centrifugal force created by rotation of the lickerin roll directs the fibers in an air stream through the conduit 120 into the pad forming chamber 14 (FIGS. 1 and 3).

Referring to FIG. 3, the pad forming chamber 14 is sealed by nylon sealing elements 122 which are connected to sidewalls defining the chamber 14. These sealing elements abut the links 46-48-50-52 during vertical travel of said links to insure that the chamber 14 is sealed to prevent air-borne fibers from escaping therefrom. The sealing elements can be formed from any suitable material capable of functioning in the above described manner.

Channel members 124 are provided for supporting the pad forming chamber 14 which is separated to provide clearance for the pad-forming run 18 of the masking frame assembly 22. The driven chains 66 are disposed outside of the pad forming chamber 14 to prevent the air borne fibers within said chamber from clogging the chain 66. Clogging of the chain would impair the operation of the apparatus.

The vacuum box 16 (FIG. 1) is mounted on the side of the masked conveyor 20 which is opposite the side that sealingly engages the masking frame assembly 22, and a vacuum is pulled through a conduit 126 (FIGS. 1 and 2) to thereby pull air through the air permeable surfaces 26 of said masked conveyor. This vacuum directs the fibers into the pad-receiving compartments of the pad-formation assembly 24 to thereby form the fibrous pads within said compartments. Since the vacuum only pulls air through the air permeable surfaces 26, there is little tendency for fibers to adhere to the air-impermeable regions 28 of the conveyor. Therefore, substantially all of the fibers directed into the pad forming chamber are utilized to form fibrous pads and are not deposited in a useless fashion on the masked portions of the conveyor 20.

Figure 6:
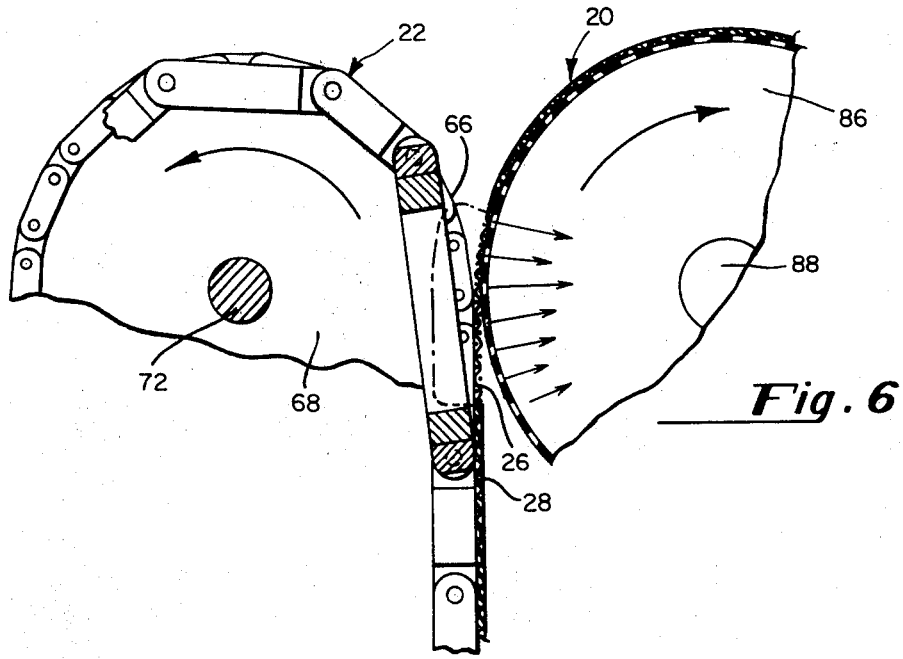
FIG. 6 is an enlarged view showing details of the separation of the masking frame assembly from the masked conveyor in an apparatus of this invention.

The vacuum box is sealed at its lower edge by a lower wall 128 and is sealed at its upper end by the driven roller 86. The driven roller 86 is perforated and provides direct air communication from the outer periphery of the roller to the vacuum box (FIGS. 1 and 6), whereby a vacuum is constantly pulled through the conveyor 20 as the side surfaces of the frame members are moved relative to the air-permeable surfaces 26 of the masked conveyor 20 by tangentially separating the masking frame assembly 22 from said masked conveyor at the upper vertical end of the pad-forming run 18 (FIG. 6). This vacuum assist assures that the formed pad will be retained on the masked conveyor, and will not tend to become distorted or destroyed because of a greater affinity of the fibrous pad for the masking frame assembly 22, than for the masked conveyor 20. By separating masking frame assembly 22 from the masked conveyor 20 the formed fibrous pads can be removed easily from the conveyor 20 onto a takeoff conveyor 129 which directs the pads in their formed spaced relationship to suitable converting equipment (not shown), whereat the individual pads can be assembled with other elements to form a finished product. For example the pads can be assembled between suitable cover sheets to form disposable diapers.

A spinnerette or fiber leveling member 130 (FIG. 1) is provided for leveling the surface of the formed fibrous pads. The spinnerette includes a plurality of projecting fingers 132 which rotate to skim the surface of the formed pads to perform the leveling operation. This structure is conventional equipment in fiber web forming machines and is well known to those skilled in the art.

Figure 7:
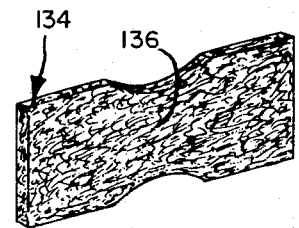
FIG. 7 is an isometric view of one product which can be produced by an apparatus of this invention.

Referring to FIG. 7, the masking frame members 32, 34 are utilized to manufacture a fibrous pad 134 having a reduced width center region 136, and which is specifically adaptable for use as an absorbent component in a disposable diaper or the like. The fibrous pad 134 can be made from 100% short cellulosic fibers of a papermaking length less than one-quarter inch, such as wood pulp fibers and second cut cotton linters, or from blends of such short fibers, and longer, reinforcing textile-length fibers.

The various frame members 32, 34 can be removed from their support members 36 and replaced with different frame members for defining different shaped openings to manufacture different shaped fibrous pads. For example, a different shaped fibrous pad may be required in a diaper which is used by a boy than in a diaper which is used by a girl. When the frame members are changed to form a different shaped pad the masked conveyor must also be changed. In the preferred embodiment of the apparatus, the opening defined by each set of frame members is identical; however, it is within the scope of this invention to utilize sets of frame members defining different shaped openings to form fibrous pads of different shapes.

The apparatus 10 of this invention can be utilized to manufacture fibrous pads of various shapes for various uses, and is extremely beneficial in applications wherein repeatable results are either desirable or necessary. Also, the apparatus 10 of this invention can include profiling masking elements between the vacuum box 16 and the pad-forming run 18 of the masking frame assembly 22 to establish a different effective volumetric air flow through different predetermined regions of the pad-receiving compartments to thereby form profiled fibrous pads. The details of the profiling features of this invention will be explained in conjunction with the following description of the second preferred embodiment of the apparatus of this invention, it being understood that such features can be employed in the apparatus 10 which has been described above.

Referring to FIG. 9, a second embodiment of an apparatus 200 is shown for forming shaped, profiled, fibrous pads. The apparatus can be utilized to form fibrous pads for many different shapes and profiles; however, the specific apparatus described in this application is utilized to manufacture shaped, profiled pads for use in different disposable diapers specifically designed for use by boy babies and girl babies, respectively. Such diapers are described in copending application Ser. No. 168,159, filed on Aug. 2, 1971, and assigned to Scott Paper Company. This latter application also discloses portions of apparatus 200, which are described hereinafter, and clearly acknowledges that the apparatus 200 is the invention of Charles G. Kolbach, who is the inventor of all of the subject matter claimed in the instant application.

The apparatus 200 has a fiberizing section 202 which includes a rotary lickerin roll 204 disposed within a formation chamber 206. The lickerin roll 204 is of conventional design, and comprises a plurality of teeth disposed about the outer periphery thereof for doffing individual fibers from sheets of pulp lap 208 and 210, and for entraining said fibers in an airstream within the formation chamber 206. If desired, only one sheet of pulp lap can be fed into the fiberizing section, or the fiberizing section can be modified to receive more than two sheets of pulp lap. Also, the fiberizing section can be utilized to blend different fibers, such as short fibers of a papermaking length less than ¼ inch, and longer reinforcing fibers of textile length.

The formation chamber 206 is closed at its downstream end by a unique, movable pad-formation assembly 212 which is disposed in an endless fashion about spaced rolls 214 and 216. At least one of the spaced rolls is driven to move the pad-formation assembly 212 in the direction indicated by arrow 218. The endless padformation assembly 212 has an upper linear pad-formation run 220, and a lower linear pad-transfer run 222. A plurality of padforming vacuum boxes 224, 226 and 228 are disposed under, and in close proximity to said pad-formation run, and function in conjunction with profiling masks in a manner which will be fully described hereinafter.

Referring to FIGS. 9 and 13, the unique pad-formation assembly 212 includes a relatively thin, open mesh conveyor 230 to which is secured a relatively thick, flexible substrate 232. Preferably the conveyor 230 is a woven member having apertures which are sufficiently small to permit retention of fibers on the upper surface thereof during the pad forming operation, while permitting the air in which the fibers are entrained to pass through the conveyor. Other conveyors can be utilized, such as nonwoven conveyors and perforated, flexible sheet conveyors. The flexible substrate 232 has a thickness in the range of from about ¼ to 1 inch and in the most preferred embodiment of this invention the substrate has a thickness of from between ½ to about ¾ inch. The flexible substrate 232 is adhered to the conveyor 230 by any suitable glue or adhesive. The flexible substrate 232 must be sufficiently flexible so that it can stretch as it turns about spaced rolls 214 and 216 without unduly stressing the conveyor 230. The imposition of undue stresses in the conveyor can cause said conveyor to crack and thereby fail.

Preferably the flexible substrate 232 is air-impermeable and has sections removed therefrom to define three-dimensional padreceiving compartments 234. Each pad-receiving compartment 234 is defined by a bottom, air-permeable surface 236 defined by the conveyor 230, and sidewall segments 238 defined by surfaces of the flexible substrate 232 provided by removing sections from said substrate.

The flexible substrate 232 can be formed from soft rubbers, such as natural rubber. Although natural rubbers are not semiconductive, the normal moisture content within the air suspension of fibers permits the dissipation of static charges from the fibers as they engage the pad-formation assembly. The flexible substrate 232 can also be formed from a foam material, such as unreticulated polyurethane foam sold by Scott Paper Company. This unreticulated polyurethane foam is air-permeable, and therefore when such a foam is utilized the regions of the conveyor underlying the foam are coated with a suitable air-impermeable substance, such as neoprene. When an air-permeable foam is utilized as the flexible substrate material, the side walls 238 also are coated with an air-impervious substance such as neoprene.

The flexible substrate 232 can be adhered to the conveyor 230 by any suitable adhesive means. In some cases, a surface of the substrate can be rendered tacky by heat or chemical treatment, and the tacky surface can provide the securing means for adhering the substrate to the conveyor. When the flexible polyurethane foam referred to above is utilized as the substrate material it can be adhered to the conveyor 230 by a polyurethane adhesive such as Bostik A and B mix (80/20) sold by Quelcor Adhesive Company of Swarthmore, Pennsylvania. All constructions of the pad-formation assembly 212 include three-dimensional pad-receiving compartments 234 having a bottom, air-permeable surface 236, and these compartments are separated from each other by air-impermeable regions which generally define a perimetrical shape corresponding to the configuration, or shape of fibrous pads to be formed.

In the preferred embodiment of this invention, the apparatus 200 includes opposed sources of vacuum 235 and 237 disposed adjacent, and outside of the downstream end of the pad-formation chamber 206. The upper vacuum source 235 is effective to remove fibers which are retained on the air-impervious regions of the pad-formation assembly 212. In these regions the partial vacuum created by the lower vacuum source 237 will have no effect since the partial vacuum cannot be established through the air-impervious regions of the pad-defining assembly. As a pad-receiving compartment 234 passes between the vacuum sources no pressure differential is created across the fibrous pads since the vacuum established through both the upper and lower vacuum boxes are substantially identical, and will cancel each other. If desired, a source of positive pressure 239 can be disposed outside of the pad-formation chamber 206 closely adjacent and outside of the upstream end thereof to blow any fibers out of the pad-receiving compartments which are retained therein from fibrous pads which previously were formed in said pad-receiving compartments.

Profiled pads are formed by positioning profiling masks between the pad-formation run 220 of the pad-formation assembly 212 and vacuum boxes 224, 226 and 228. These profiling masks prevent the passage of air through the bottom air-permeable surface 236 of each pad-receiving compartment 234 in different predetermined sections thereof along the linear pad-formation run 220 of the pad-formation assembly 212 to establish a different effective volumetric air flow in said different predetermined sections to direct different weights of fibers into said different predetermined sections.

Referring to FIG. 12, a fibrous layer 242 in the form of a shaped, profiled fibrous pad is shown which can be formed by utilizing the apparatus of FIG. 9. This fibrous pad has a substantially hour-glass shape defined by a reduced width middle region 244. A greater weight of fibers per unit area is disposed in the middle region 244 than in opposed end regions 246 and 248. The weight of fibers per unit area in each of the end regions 246 and 248 is substantially identical. An exemplary fibrous layer 242 has a middle region 244 with a basis weight of approximately 30 oz/yd$^2$, and end regions 246 and 248 with a basis weight of approximately 20 oz/yd$^2$. This fibrous pad 242 is utilized specifically in a diaper adapted to be used by a girl baby, as is more fully described in copending U.S. application Ser. No. 168,159, which was referred to earlier in the instant application.

Referring to FIG. 13, the fibrous pad 242 is formed by disposing profiling masks 250, 252 and 254 between the pad formation run 220 of the pad-formation assembly 212 and the pad forming vacuum boxes 224, 226 and 228, respectively. The profiling mask 250 has an open mesh, air-permeable elongate center region 256, and air-impermeable elongate end regions 258 and 260. The profiling mask 252 also has an open mesh, air-permeable elongate center region 262, and air-permeable elongate end regions 264 and 266. The profiling mask 254 has an air-impermeable elongate center region 268, and open mesh, air-permeable elongate end regions 270 and 272.

The pad-forming vacuum boxes 224, 226 and 228 are connected to an exhaust fan, or similar exhaust device (not shown), through connecting conduits 274 (only one of which is shown in FIG. 13). Each connecting conduit 274 can be provided with a valve therein to control the volume of air which is pulled through its associated vacuum box by the exhaust device. Alternatively, the valves can be omitted, and separate exhaust devices can be connected to each of the vacuum boxes to control independently the volume of air pulled through each vacuum box. When the volumetric air demand through each vacuum box is to be the same, a single exhaust device can be employed, and the valves in conduits 274 can be omitted. However, for purposes of equipment versatility, each of the connecting conduits 274 is provided with a regulating valve therein so that the volumetric air demand through each vacuum box can be independently controlled.

To form the fibrous pad 242 shown in FIG. 12, the padformation assembly 212 is driven at a substantially constant speed sequentially over the profiling masks 250, 252 and 254 in the direction indicated by arrow 218 in FIGS. 9 and 13. Referring to FIGS. 9, 14A and 14B, the air suspension of fibers is divided essentially into separate streams 276, 278 and 280 by the application of a partial vacuum through the pad-receiving compartments 234 which overlie the vacuum boxes 224, 226 and 228, respectively. The vacuum boxes 224 and 226 are effective to direct the fiber streams 276 and 278, respectively, into substantially only a middle section 279 of each pad-receiving compartment 234, as each compartment passes over said vacuum boxes (FIGS. 14A and 14B). The fiber streams 276 and 278 are directed substantially only into the middle section 279 of each compartment because the elongate end regions of the profiling masks 250 and 252 overlie the vacuum boxes 224 and 226 to prevent the fiber streams from being drawn into the end sections of the pad-receiving compartment 234. Referring to FIGS. 14A and 14B, some dusting of fibers occurs in the end sections 281 and 283 of each pad-receiving compartment 234 during the formation of the middle region 244 of the fibrous pad 242; however, this dusting of fibers is of an extremely low basis weight, i.e. less than 1 oz/yd$^2$, and has relatively little, if any, effect on the resistance of air flow through the end sections of the pad-receiving compartment. Therefore this dusting of fibers does not influence significantly the subsequent formation of the end regions 246 and 248 of the fibrous pad 242. Therefore, the middle region 244 of the fibrous pad 242 is formed completely and substantially independently of the formation of end regions 246 and 248 of the fibrous pad.

Referring to FIGS. 9, 13 and 14C, the fiber stream 280 is directed substantially only into end sections 281 and 283 of each pad-receiving compartment 234 as each pad-receiving compartment passes over the vacuum box 228 to thereby form the end regions 246 and 248 of the fibrous pad 242 completely and substantially independently of the formation of the middle region 244 of the fibrous pad. This formation of the end regions 246 and 248 is effected by masking the vacuum box 228 to the passage of air by the elongate center region 268 of the profiling mask 254 in a region directly underlying the center section 279 of the padreceiving compartment 234. Some dusting of fibers may occur in the middle region 244 of the fibrous pad during the passage of each pad-receiving compartment over the vacuum box 228; however, this dusting of fibers is substantially inconsequential, and does not have any significant effect on the basis weight of the previously formed middle region 144 of the fibrous pad.

Since the middle section 279 of each pad-receiving compartment 234 is exposed to a partial vacuum for a greater length of time than the end sections 281 and 283, the profiled, fibrous pad 242 having a greater weight of fibers per unit area in the middle region 244 than in the end regions 246, 248 can be formed by establishing the same volumetric air demand through all of the vacuum boxes by either one or more vacuum creating sources connected to said vacuum boxes. Different effective volumetric air flows can be established in different predetermined sections of the pad-receiving compartments by any of the means set forth earlier in this application to form a fibrous pad having predetermined regions, each of which has a different weight of fibers per unit area therein. The specific volumetric air demand through each of the vacuum boxes, and the time of exposure of different predetermined sections of a pad-receiving compartment to a partial vacuum can be varied to form many different profiled, fibrous pads, and these parameters are easily determinable by a person skilled in the art. The critical criteria in setting the above parameters is to prevent excessive compaction of the fibers in a predetermined section of each pad-receiving compartment which will prevent air from passing through said predetermined section prior to the complete formation of the region of the fibrous pad formed in said predetermined section. If air is prevented from passing through a partially formed region of the pad, fibers will not be deposited in said region to complete its formation.

Figure 15:
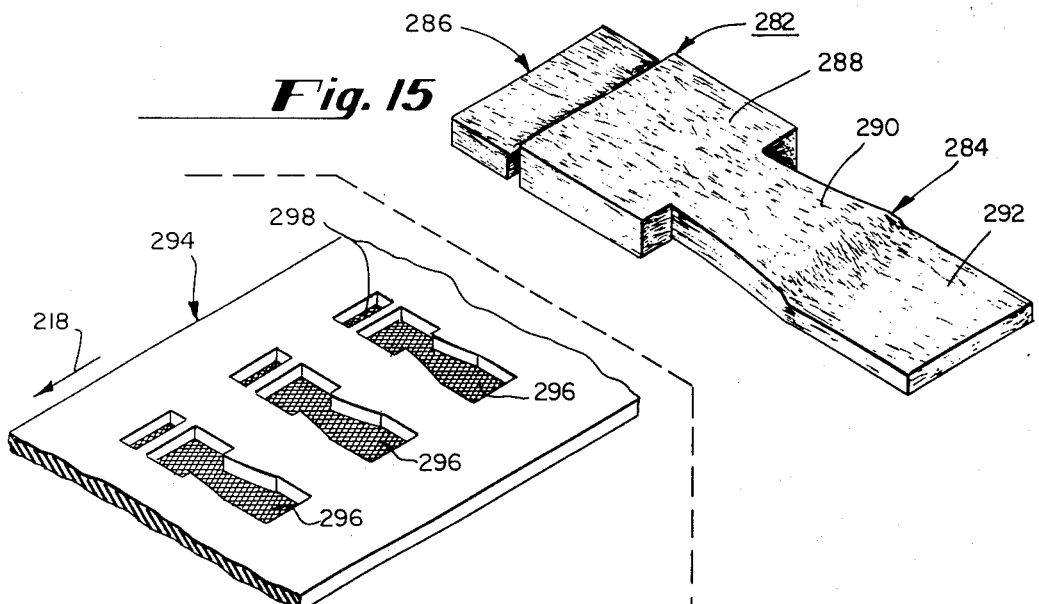
FIG. 15 is an isometric view of a different fibrous pad which can be manufactured by the apparatus of FIG. 9.

Referring to FIG. 15, a fibrous layer 282 can be manufactured by employing the method and apparatus of this invention in which the pad-formation assembly and the profiling masks are different than those employed to form the fibrous pad 242 shown in FIG. 12. The fibrous layer 282 includes a main fibrous pad 284 and a secondary fibrous pad 286. The main fibrous pad has a forward end region 288 with the greatest weight of fibers per unit area therein, e.g. over 30 oz/yd$^2$. A middle region 290 of the main fibrous pad has a lesser weight of fibers per unit area therein, e.g. 20 oz/yd$^2$, than the forward end region, and the secondary fibrous pad 286 has the same weight of fibers per unit area therein as the middle region 290. A rearward end region 292 of the main fibrous pad has the least weight of fibers per unit area therein, e.g. 17 oz/yd$^2$. The above-described absorbent layer 282 is specifically adapted for use as an absorbent component in a disposable diaper designed for boy babies, as is more fully described in copending U.S. Patent Application Ser. No. 168,159, which was referred to earlier in this application.

Figure 16:
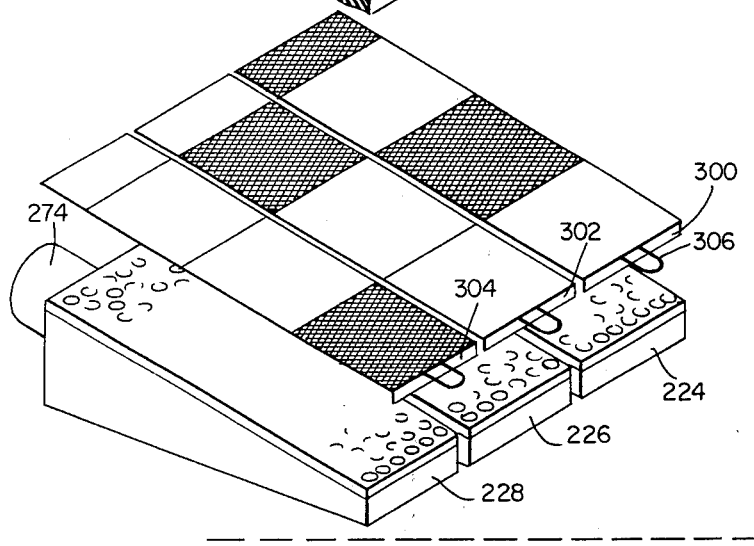
FIG. 16 is an exploded isometric view of portions of the apparatus of FIG. 9 utilized to manufacture the fibrous pad shown in FIG. 15.

Referring to FIG. 16, a pad-formation assembly 294 for forming the fibrous layer 282 includes main pad-receiving compartments 296 and secondary pad-receiving compartments 298 which are in transverse alignment with the main pad-receiving compartments. Profiling masks 300, 302 and 304 are disposed over the vacuum boxes 224, 226 and 228, respectively; and the pad-formation assembly is directed at a substantially constant speed sequentially over these masked, vacuum boxes in the direction indicated by arrow 218. The main fibrous pad 284 is formed in each of the main pad-receiving compartments 296, and the secondary fibrous pads 286 are formed in each of the secondary pad-receiving compartments 298. The preferred method of forming the fibrous layer 282 is identical to the preferred method of forming the fibrous layer 242 shown in FIG. 12. This preferred method involves the forming of predetermined regions of the fibrous pad having the same weight of fibers per unit area therein completely and substantially independently of the formation of every other predetermined region having a different weight of fibers per unit area therein.

Figure 17A:
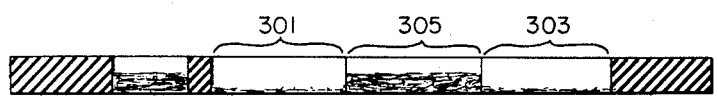
FIGS. 17A 17B and 17C show the cross sectional profile of the fibrous pad shown in FIG. 15, during sequential stages of formation according to the preferred method of this invention.

Referring to FIGS. 16 and 17A, the secondary fibrous pad 286 and the middle region 290 of the main fibrous pad are formed as the transversely aligned main and secondary pad-receiving compartments pass over the vacuum box 224. The vacuum box 224 is masked to prevent the passage of air through the forward and rearward end sections 301 and 303, respectively, of each of the main pad-receiving compartments 296. Some minor dusting of fibers occurs in the forward and rearward end sections 301 and 303 of each main pad-receiving compartment as it passes over the vacuum box 224; however, as explained earlier in this application, this dusting of fibers has substantially little, if any, effect on the resistance to air flow through said forward and rearward end sections of the pad-receiving compartments during the subsequent formation of said forward and rearward end regions 288 and 292, respectively, of the main fibrous pad 284.

Figure 17B:

Referring to FIGS. 16 and 17B, the middle region 290 of the main fibrous pad 284 is formed in a middle section 305 of each main pad-receiving compartment 296, as each of said compartments 296 pass over the vacuum box 226. The vacuum box 226 is masked to prevent the passage of air through all sections of the main and secondary pad-receiving compartments except the middle section 305. Again, some fine dusting of fibers may occur in other sections of the pad-receiving compartments as said compartments pass over the vacuum box 226; however, this dusting of fibers is virtually inconsequential, and does not influence, to any significant extent, the subsequent formation of other regions of the fibrous layer 282.

Figure 17C:
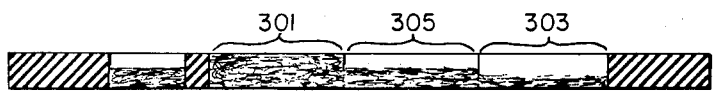

Referring to FIGS. 16 and 17C, the rearward end region 292 of the main fibrous pad 284 is completely formed within a rearward end section 303 of each main pad-receiving compartment 296, as each of said compartments passes over the vacuum box 228. The vacuum box 228 is masked to prevent the passage of air therethrough in all regions except the region underlying the rearward end section 303 of each main pad-receiving compartment 296.

In forming the fibrous layer 282 all sections of the padreceiving compartments are exposed to a partial vacuum for the same length of time. Therefore, a different effective volumetric air flow is established through sections of the pad-receiving compartments by creating a different volumetric air demand through each of the vacuum boxes 224, 226 and 228, respectively. It is within the purview of this invention to include additional vacuum boxes and additional masking means, depending upon the specific weight of fibers per unit area which is to be included in a given region of the fibrous layer. It is also within the purview of this invention to establish different effective volumetric air flows by any of the methods set forth earlier in this application. The criteria which must be met in forming fibrous pads according to the most preferred method of this invention is that each region which has a specific weight of fibers per unit area therein must be formed completely and substantially independently of the formation of every other region having a different weight of fibers per unit area therein. Also, as explained above, the parameters of time of exposure to the partial vacuum, and the specific volumetric air demand established through the vacuum boxes must be such as to permit the deposition of the desired weight of fibers per unit area in a given region without excessively matting the fibers into a dense matt through which air will not pass prior to the complete formation of said given region.

Referring to FIGS. 13 and 16, each of the profiling masks is provided with a handle 306, or other similar grasping means, adjacent one end thereof to permit easy removal of each mask when it is desired to substitute a different mask therefor, or when it is desired to eliminate the masks. By substituting or omitting profiling masks, the apparatus 200 can be utilized to form many different profiles of absorbent pads, or to form shaped, unprofiled pads.

In manufacturing throw-away diapers for use by girl babies and boy babies, the method and apparatus for positioning the formed absorbent pads between opposed cover layers is identical. Therefore, the following description will be limited to the method and apparatus of positioning the fibrous pad 242 (FIG. 12) between opposed cover layers for manufacturing disposable diapers specifically adapted for use by girl babies.

Referring to FIGS. 9 and 10, the fibrous pads 242, in the form of fluff batts of cellulosic fibers of papermaking length, have an exposed upper surface which is leveled by the teeth, or bristles of a rotating spinnerette 308 disposed at the downstream exit end of the formation chamber 206. The fibrous pads are then directed about the roll 214 where they are contacted by a cover layer 310 which is directed against the pad-formation assembly 212 by an idler roll 308. The cover layer 310 cooperates with the pad-formation assembly to confine the fibrous pads 242 within their respective pad-receiving compartments. The cover layer 310 is moved in synchronism with the pad-formation assembly 212 to a position in engagement with the lower, transfer run 222 thereof. The cover layer 310 also is supported by an upper pad-receiving run 312 of a transfer conveyor 314. The cover layer 310 and the overlying fibrous pads are fed on the transfer conveyor 314 over a transfer vacuum box 315 disposed directly under the upper, padreceiving run 312 of said transfer conveyor. A partial vacuum is applied through the vacuum box 315 to create a pressure differential across the fibrous pads 242 to transfer allegience of said pads from the pad-transfer run 222 of the pad-formation assembly 212 to the pad-receiving run 312 of the transfer conveyor 314. This partial vacuum is applied through the cover layer 310, which is a fibrous air-pervious web, and the fibrous pads 242 are relatively thick and thereby prevent the air drawn through the vacuum box from being drawn easily through said fibrous pads. In this manner, the above-described pressure differential is established across the fibrous pads. This pressure differential is maintained on the fibrous pads as the pad-formation assembly 212 commences to turn about the support roll 216 at the downstream end of the transfer run 222 to thereby separate the transfer run from the pad-receiving run 312 of the transfer conveyor 314.

Referring to FIG. 11, separation of the fibrous pads 242 from the pad-formation assembly 212 is enhanced by the movement of a sidewall section defined by the flexible substrate 232 relative to the bottom surface 236 and the other sidewall sections as the pad-formation assembly 212 is stretched about the support roll 216. The new position of the sidewall section is indicated in FIG. 11 by the numeral 238' and functions to open the compartment and permit the fibrous pad to be separated easily from the compartment without damaging or distorting the shape of said pad. The fibrous pads 242 are disposed on the cover layer 310 as said cover layer is fed off the the transfer conveyor 314. Adhesive is applied to the upper exposed surface of the cover layer 310 in regions disposed between adjacent fibrous pads at a suitable adhesive station, indicated schematically at 316. An opposed cover layer 318, which can be fluid-pervious or fluid-impervious, is superimposed over the spaced fibrous pads downstream of the adhesive station to form a composite structure consisting of the fibrous pads and the opposed cover layers. The composite structure is then fed to subsequent finishing stations (not shown) whereat the composite structure is formed into individual throw-away diapers by severing and folding in any desired manner, as is well known in the art.

What is claimed is:

1. A method for forming individual, spacedapart fibrous pads which have different predetermined regions having different weights of fibers per unit area therein, and for conveying the pads to a subsequent processing operation, said method comprising the steps of:
    A. entraining fibers in air to form an air-suspension of fibers within a formation chamber;
    B. closing one end of the formation chamber with a forming fun of an moving pad-formation assembly to provide a forming area on the forming run in underlying relationship with the formation chamber, said assembly having a plurality of spaced, three-dimensional pad-receiving compartments therein, each pad-receiving compartment being defined, in part, by a bottom air-permeable surface, said pad-formation assembly including a substantially linear pad-transfer run opposed to said forming run;
    C. establishing a first effective volumetric air flow through a first predetermined section of each pad-receiving compartment of the forming run as each compartment passes the formation chamber to form said one predetermined region of said pad;
    D. establishing a second effective volumetric air flow which is different than said first effective volumetric air flow through a second predetermined section of each padreceiving compartment in the forming run as each compartment passes the formation chamber to form said at least one other predetermined region of said fibrous pad;
    E. directing the formed pads out of said forming area on the pad-formation assembly and to the pad-transfer run of said assembly;
    F. directing a linear pad-receiving run of a padtransfer conveyor means generally parallel to the substantially linear pad-transfer run of the pad-formation assembly; and
    G. establishing a partial vacuum through said padreceiving run for transferring allegiance of the formed fibrous pads from the pad-transfer run of the pad-formation assembly to the pad-receiving run of the pad-transfer conveyor means.

2. The method according to claim 1, including the step of directing an air-permeable, absorbent fibrous web between the padtransfer run of the pad-formation assembly and the pad-receiving run of the pad-transfer conveyor means, whereby said partial vacuum is effective to transfer allegience of the formed fibrous pads to the air-permeable fibrous web.

3. The method according to claim 2, including the step of directing the pad-transfer run of the pad-formation assembly away from the pad-receiving run of the pad-transfer conveyor means at a downstream end of the pad-transfer run, and maintaining said partial vacuum through the pad-receiving run of the pad-transfer conveyor means during said separation to retain the forward fibrous pads on the air-permeable web.

4. The method according to claim 3, including establishing a spacing between the pad-transfer run of the pad-formation assembly and the pad-receiving run of the pad-transfer conveyor means to prevent substantial movement of the fibrous pad relative to said pad-transfer run and said pad-receiving run as the allegience of said formed fibrous pads for said air-permeable web is established.

5. A method for forming individual, spacedapart fibrous pads and for conveying said pads to a subsequent processing operation, said method comprising the following steps:
    A. entraining fibers in air to form an air-suspension of fibers within a formation chamber;
    B. closing an end of said formation chamber with a substantially linear forming run of a moving pad-formation belt means to form a pad forming area in underlying relationship with the formation chamber, said pad-formation belt means being endless and having a substantially linear padtransfer run opposed to said forming run, said pad-formation belt means futher including a plurality of spaced-apart groups of small apertures extending through opposed surfaces, each group of apertures corresponding to the desired configuration of a fibrous pad which is to be formed and constituting a bottom surface of a three-dimensional compartment;
    C. establishing a pressure drop through the groups of apertures in the pad forming area to pull fibers from the air-suspension into each three-dimensional compartment to form the spaced-apart pads with well-defined shapes;
    D. directing the formed pads out of said forming area on the pad-formation belt means and to the pad-transfer run of said belt means;

E. directing a linear pad-receiving run of a pad-transfer conveyor means generally parallel to the pad-transfer run of the pad-formation belt means; and F. establishing a pressure drop through said pad-receiving run for transferring allegiance of the formed fibrous pads from the pad-transfer run of the pad-formation belt to the pad-receiving run of the pad-transfer conveyor means, said conveyor means being adapted to direct the formed pads to subsequent processing operations.

6. A method for forming discrete fibrous pads which have different predetermined regions, the weight of fibers per unit area in one predetermined region of each pad being different than the weight of fibers per unit area in at least one other predetermined region, said method comprising the steps of:

A. separating fibers from a web and entraining said fibers in air to form an air-suspension of fibers within a formation chamber;

B. enclosing one end of the formation chamber with a forming run of a moving pad-formation assembly having a plurality of spaced, three-dimensional pad-receiving compartment therein, each pad-receiving compartment being defined, in part, by a bottom air-permeable surface, and said pad-receiving compartments being separated from each other by air-impervious regions of said assembly;

C. establishing first and second effective volumetric air flows which are different from each other through first and second predetermined sections, respectively, of each pad-receiving compartment for directing different quantities of the air-suspension of fibers into said first and second predetermined sections of each pad-receiving compartment to form said one predetermined region of the fibrous pad and said at least one other predetermined region of the fibrous pad, said first and second effective volumetric air flows being established by either one of the following means;

1. establishing the same volumetric demand for air per unit time, for different lengths of time, by sucking the air through a vacuum means positioned underneath each pad-receiving compartment, or 2. establishing a different volumetric demand for air per unit time, for the same or different length of time, by sucking the air, through a vacuum means position underneath each pad-receiving compartment.

7. The method according to claim 6, including establishing said first and second volumetric air flows during nonoverlapping time periods in non-overlapping sections of each pad-receiving compartment.

8. The method according to claim 6, including the step of forming said pad-formation assembly with air-impervious regions having surfaces extending out of the general plane of the bottom air-permeable surfaces for defining side walls of the three-dimensional pad-receiving compartments, said first and second effective volumetric air flows being effective for directing fibers substantially only into said pad-receiving compartments.

* * * * *